United States Patent [19]
Underwood et al.

[11] Patent Number: 5,696,328
[45] Date of Patent: Dec. 9, 1997

[54] SELF TIGHTENING CLAMP

[75] Inventors: Jeffery D. Underwood, Raleigh; Thomas E. Andrews, Creedmoor; Waite R. Warren, Jr., Raleigh, all of N.C.

[73] Assignee: Mitsubishi Semiconductor America, Inc., Durham, N.C.

[21] Appl. No.: 720,498

[22] Filed: Sep. 30, 1996

[51] Int. Cl.⁶ .................................................. G01N 3/02
[52] U.S. Cl. ............................ 73/856; 73/860; 269/234
[58] Field of Search ............................ 73/856, 857, 858, 73/859, 860; 269/234, 238, 232

[56] References Cited

U.S. PATENT DOCUMENTS

| | | |
|---|---|---|
| 1,162,059 | 11/1915 | Hersey .......................... 269/234 |
| 2,707,835 | 5/1955 | Gierlich ........................ 269/234 |
| 2,722,250 | 11/1955 | Applegate ...................... 269/234 |
| 3,988,865 | 11/1976 | Weisman ........................ 269/234 |

*Primary Examiner*—Ronald L. Biegel
*Assistant Examiner*—Max H. Noori
*Attorney, Agent, or Firm*—Lowe, Price, LeBlanc & Becker

[57] ABSTRACT

A clamp assembly for holding an object includes a first clamp member having a first grip portion and a second clamp member having a second grip portion disposed opposite said first grip portion. A first guide member restricts the first clamp member to movement along a first axis and a second guide member restricts the second clamp member to movement along a second axis, the second axis being disposed so as to cross the first axis at a crossover point.

22 Claims, 5 Drawing Sheets

SELF TIGHTENING CLAMP

TECHNICAL FIELD OF THE INVENTION

The present invention relates to clamps and more particularly to an automatically self tightening clamp.

BACKGROUND OF THE RELATED ART

Clamping devices in numerous configurations are used for various purposes. Typically, the clamping device must securely grip the object being clamped so that the object can be moved or restrained from movement.

One use of clamping devices is to grip test specimens so that forces can be applied to verify the strength of a manufactured object. In devices used for this purpose, the physical testing apparatus may include one or more clamp assemblies to grip one or more points on the test specimen. Once the clamp assembly or assemblies have been set, the test specimen is subjected to a force, such as a tensile or compression force, to determine physical properties of the test specimen.

Clamp assemblies are often used in peel or tear testing metal sheets which have been joined together by welding. To quality inspect the compound sheets, the strength of the weld can be tested by making cuts in the two joined sheets to expose tongues of the sheet material. The tongues are gripped and bent over until the material is destroyed to determine if the rupture point is in the tongue or the weld and thereby judge the quality of the welded seam.

OBJECTIVES OF THE INVENTION

It is an objective of the present invention to provide an improved clamping device for gripping test specimens during quality testing.

It is another objective of the present invention to provide an improved clamping device which is suitable for use in peel testing a test specimen.

It is also an objective of the present invention to provide a clamping device which increases its grip as the force on the gripped object increases.

It is yet another objective of the present invention to provide a clamping device which is simple to operate and can be easily engaged to and disengaged from the gripped object.

It is a further objective of the present invention to provide a clamping device which is capable of use for both tensile and compression testing of test specimens.

Additional objects, advantages and novel features of the present invention will become apparent to those skilled in the art from this disclosure, including the following detailed description, as well as by practice of the invention. While the invention is described below with reference to a preferred embodiment(s), it should be understood that the invention is not limited thereto. Those of ordinary skill in the art having access to the teachings herein will recognize additional implementations, modifications and embodiments which are within the scope of the invention as disclosed and claimed herein, and with respect to which the invention could be of significant utility.

SUMMARY OF THE INVENTION

In accordance with the invention, a clamp assembly for holding an object includes a first clamp member having a first grip portion or jaw and a second clamp member having a second grip portion or jaw which is disposed opposite the first grip portion. A first guide member restricts movement of the first clamp member to linear movement along a first axis and a second guide member restricts movement of the second clamp member to linear movement along a second axis. The guide members are arranged such that the second axis crosses the first axis at a crossover point. If the two guide members are in the same plane, the crossover point will be at the intersection of the two axes. Advantageously, the second axis crosses the first axis at an angle of approximately 60 degrees, however other angular displacements could be used if desired. The first and second clamp members are configured to slide on the first and second guide members. Beneficially, the first and second guide members are fixedly connected to a base, which can be stationary or movable.

According to other aspects of the invention, a first elastic member, such as a metal spring, is connected to the first clamp member so as to apply a force to urge the first clamp member to slide along the axis of the first guide member towards the crossover point. A second elastic member, such as another metal spring, is connected to the second clamp member and also applies a force to urge the second clamp member to slide along the axis of the second guide member towards the crossover point. In this way, the first and second elastic members cause said first and second grip portions to be automatically placed and remain in contact when the clamp assembly is not in use, e.g. during storage, and to automatically engage an object placed between the opened grip portions of the clamp members.

Movement of the first and second clamp members on the guide members towards said crossover point decreases the distance between the first and second grip portions. Hence, the grip on the clamped object automatically increases as a force, e.g. a tension or compression force, in the direction of the crossover point is initially applied to the clamped object or is increased. This holds true whether the grip portions have toothed or friction grips, or some other type of gripping surface.

In accordance with still further aspects of the invention, first and second ear members are respectively connected to or formed as an integral part of the first and second clamp members. The ear members are configured to receive a force which urges the first clamp member to slide along the axis of the first guide member away from the crossover point and a force which urges the second clamp member to slide along the axis of the second guide member away from the crossover point. Accordingly, the first grip portion will separate, or further separated if already separated by a clamped object, from said second grip portion, i.e. the grip portions will be moved further apart when force is applied to the ear members, to release a clamped object or to allow an object to be placed between the grip portions prior to clamping.

To clamp an object, the object is placed between the opposed grip portions of the first and second clamping members. The spring loading of the first and second clamping members will cause the first and second grip portions to initially engage the object. A force, typically a tension or compression force in the direction of the crossover point, applied to the object will cause simultaneous linear movement of the first clamping member to slide along the axis of the first guide member and of the second clamping member to slide along the axis of the second guide member. The movement of the first and second clamping members will be towards the crossover point of the first and the second axes. The simultaneous linear movement of the first and second clamping members will result in the first and second grip portions applying an increased gripping force on the object.

To release the clamped object, release forces are applied to the first and second clamping members in a direction substantially opposite to the direction of the force on the clamped member, i.e. in a direction away from the crossover point. The release forces will cause each clamping member to slide along the axis of its associated guide member. This will result in the simultaneous linear movement of the first clamping member and of the second clamping member away from the crossover point of the axes. In this way the clamp can be easily released and the object can be easily removed from the clamp.

DETAILED DESCRIPTION OF THE PREFERRED EMBODIMENTS

Figure 1:
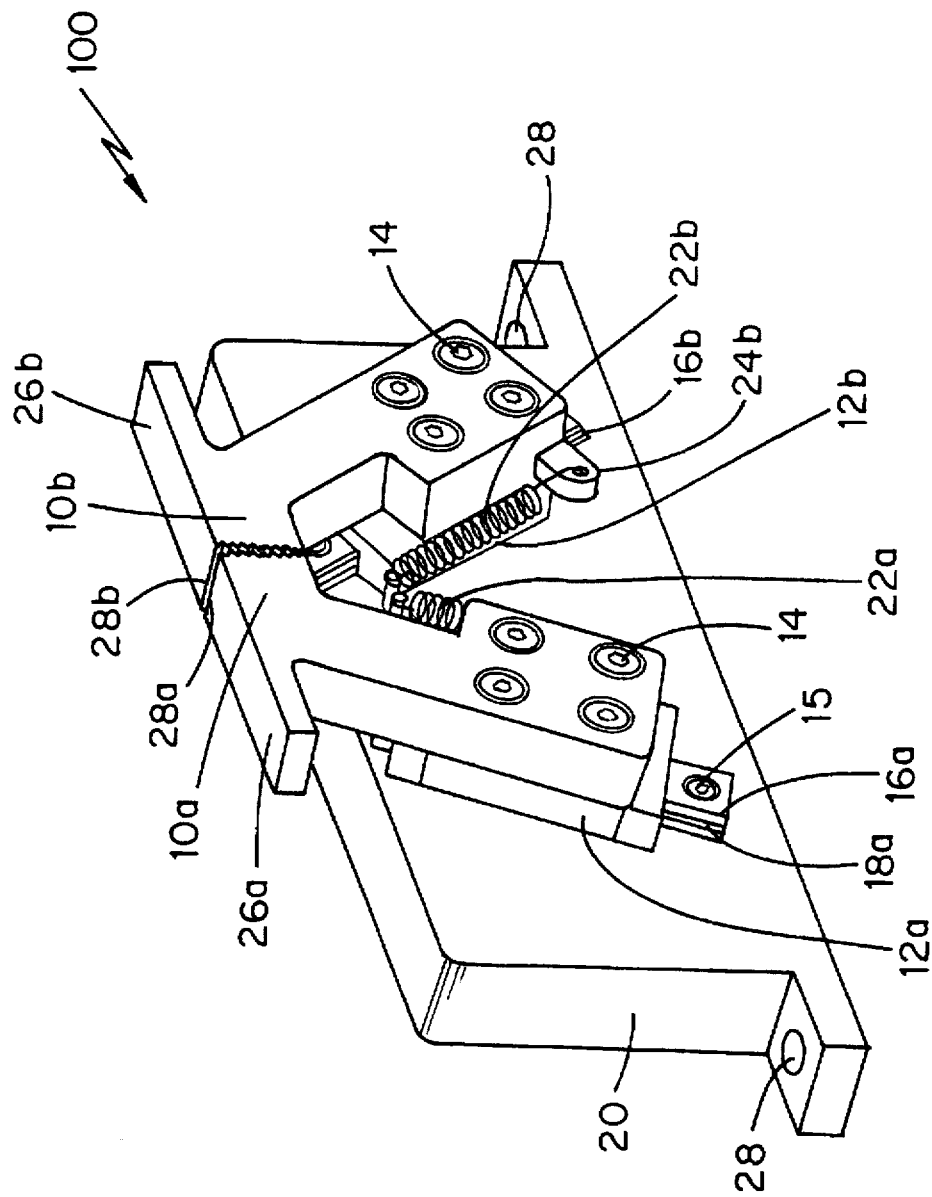
FIG. 1 is a perspective view of a clamp assembly in accordance with the present invention.

FIG. 1 is a perspective view of a clamp assembly 100 in accordance with the present invention. As depicted, the clamp assembly 100 includes clamp members 10a and 10b which are formed of high strength steel, but could be formed of any other rigid or semi-rigid material suitable for the intended implementation. The clamp members 10a and 10b are respectively attached to plates 12a and 12b using countersunk threaded connectors 14. It should also be noted that each of the clamping members 10a and 10b and its associated plate 12a or 12b could be formed integrally or could be welded together.

The plates 12a and 12b are also formed of high strength steel but could be formed of another rigid or semi-rigid material capable of withstanding the forces to which the plate will be subjected during the gripping of an object. Each of the plates 12a and 12b includes a groove which is configured to accept a flange, such as flange 18a, of one of the linear motion guide members 16a and 16b. The guide members 16a and 16b, as shown, are formed of high strength steel but could, if desired, be formed of another material. The guide member flanges, such as flange 18a, hold the plates 12a and 12b and hence the clamping members 10a and 10b adjacent to the mounting base 20 to which the linear movement guides 16a and 16b are connected by countersunk threaded connectors 15. The linear movement guides could alternatively be welded rather than bolted to the base 20.

To maintain the clamping member jaws 28a and 28b together when the clamp assembly is not in use, and to initiate engagement of an object to be gripped, springs 22a and 22b are provided. Each spring has one end connected to a flange, for example 24b, on its associated clamp member and another end connected to the base 20. The connection to the base 20 can be implemented in any desired manner so long as the strength of the connection is sufficient to withstand the tension force on the applicable spring 22a or 22b.

It will be recognized that the springs could be replaced by another type of elastic member, such as one formed of rubber, if desired. The springs are sized so as to always be in tension and are selected so that the tension increases as the jaws 28a and 28b are separated, although this is not a mandatory requirement.

Each of the clamping members 10a and 10b is provided with an ear 26a or 26b, one or both of which can be pressed to separate the jaws 28a and 28b of the respective clamping members 10a and 10b in order to place the object to be gripped between the jaws 28a and 28b or to release a gripped object from the jaws 28a and 28b.

As shown in FIG. 1, the base 20 includes mounting holes 28 which can be used to mount the base to a structural support. Alternatively, the base may be an integral part of or welded to a structural support. In either case, the structural support should have sufficient strength or mass to resist all loads which may be generated on the clamp assembly. It will, of course, be recognized that the clamping members could be installed on a hand-held base in which case, the holes 28 would not be required.

Figure 2:
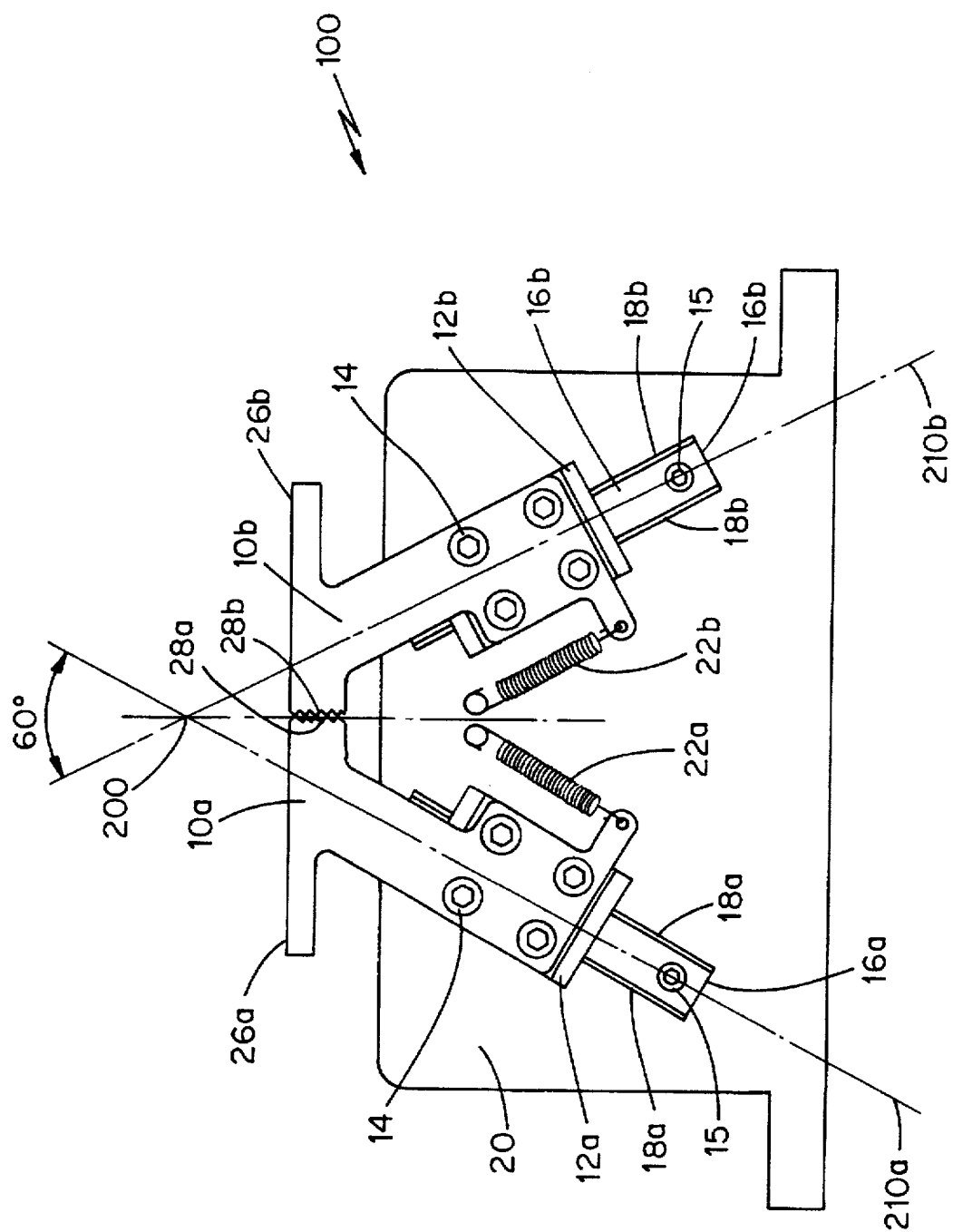
FIG. 2 is a front view of the clamp assembly depicted in FIG. 1.

Turning now to FIG. 2, a front view of the clamp assembly depicted in FIG. 1 is shown. As indicated in FIG. 2, flanges 18a and 18b extend from both side edges of the linear movement guides 16a and 16b. The serrated clamp jaws 28a and 28b provide a positive grip on an object. As shown in FIG. 2, the threaded fasteners 14 and 15 are preferably threaded socket head fasteners which are countersunk so as not to protrude from the surface of the clamping members 10a and 10b or the linear movement guides 16a and 16b.

The guide axes 210a and 210b intersect at a point 200. The axes of the guides are separated by an angle of approximately 60°. Although the axes 210a and 210b must cross, the angular separation may differ depending on the desired implementation. Preferably, the crossover point is centered between the clamping members 10a and 10b as shown.

To operate the clamping assembly 100, a force directed away from the crossover point 200, e.g. downward in FIG. 2, is applied to each of ears 26a and 26b. Because the force is directed away from point 200, at least a component of the force will be along an applicable axis of one of the linear movement guides 18a and 18b. The forces urge the respective clamping members 10a and 10b to slide along the guide members 16a and 16b away from point 200 thereby opening the jaws 28a and 28b to accommodate an object to be gripped. The tension on springs 22a and 22b is increased by the movement of the clamping members 10a and 10b away from point 200.

After the object has been placed between the jaws 28a and 28b, the force on the ears 26a and 26b is released. Springs 22a and 22b, which have been stretched by the movement of the clamping members 10a and 10b along the guides 16a and 16b, apply forces in directions substantially parallel to the axes of the linear movement guides 16a and 16b to urge the clamping members 10a and 10b to slide on guides 16a and 16b towards point 200 and into engagement with the object to be gripped. Because of the force applied by the springs 22a and 22b, a strong grip is established on the object by the jaws 28a and 28b upon engagement.

As a force is applied to the gripped object in the direction of point 200, the clamping members 10a and 10b will simultaneously slide along the linear movement guides 16a and 16b towards the point 200. This movement will cause the separation between the jaws 28a and 28b to decrease and thereby tighten the grip on the clamped object. The greater the force applied to the clamped object, the greater will be the movement of the clamping members 10a and 10b along the guides 16a and 16b towards the point 200 and accordingly, the greater the grip of the jaws 28a and 28b on the object.

To release the object from the clamp assembly 100, a force is again applied to one or both of the ears 26a and 26b to urge the clamping members 10a and 10b to slide on linear movement guides 16a or 16b away from the point 200 and thereby open the jaws 28a and 28b. Thus, the gripped object can be easily released and removed from the clamp assembly 100.

Figure 3:
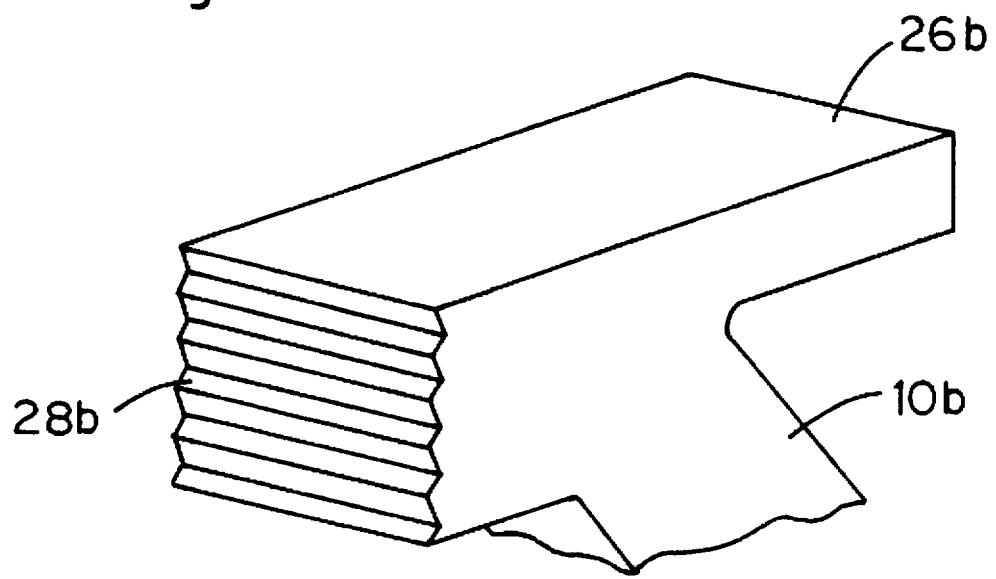
FIG. 3 is a detail of a serrated type jaw which could be incorporated in the clamp assembly depicted in FIG. 1.

Turning now to FIG. 3, an enlarged view of the jaw 28b and ear 26b of the clamping member 10b is depicted in a perspective view. As shown, the serrated type jaw 28b and ear 26b are integrally formed as part of the clamping member 10b. This however, is not mandatory and the ear and jaw could be removably mounted to the clamping member 10b, if desired.

Figure 4:
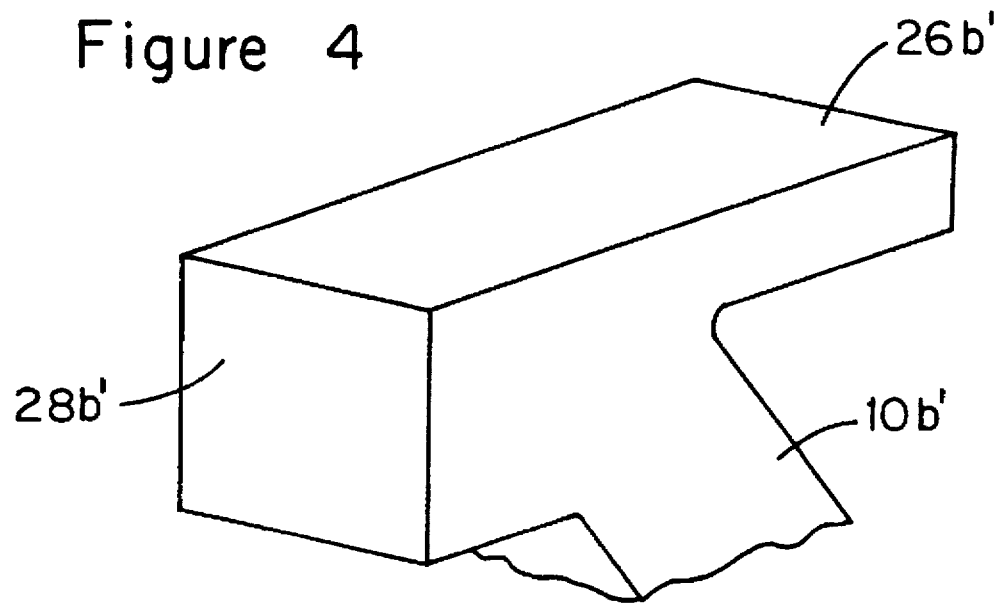
FIG. 4 depicts a smooth type jaw which could be incorporated in the clamp assembly shown in FIG. 1.

FIG. 4 depicts a clamping member 10b' which includes an ear 26b' and a smooth friction type jaw 28b'. Except for the substitution of a smooth gripping surface for the serrated gripping surface of jaw 28b, the clamping members 10b and 10b' are identical. The friction type jaw 28b' could be formed of high strength steel or some other rigid or semi-rigid material or could alternatively have its gripping surface formed of a flexible material such as rubber or plastic. In general, any material or type of surface can be utilized as may be suitable for the particular implementation.

Figure 5:
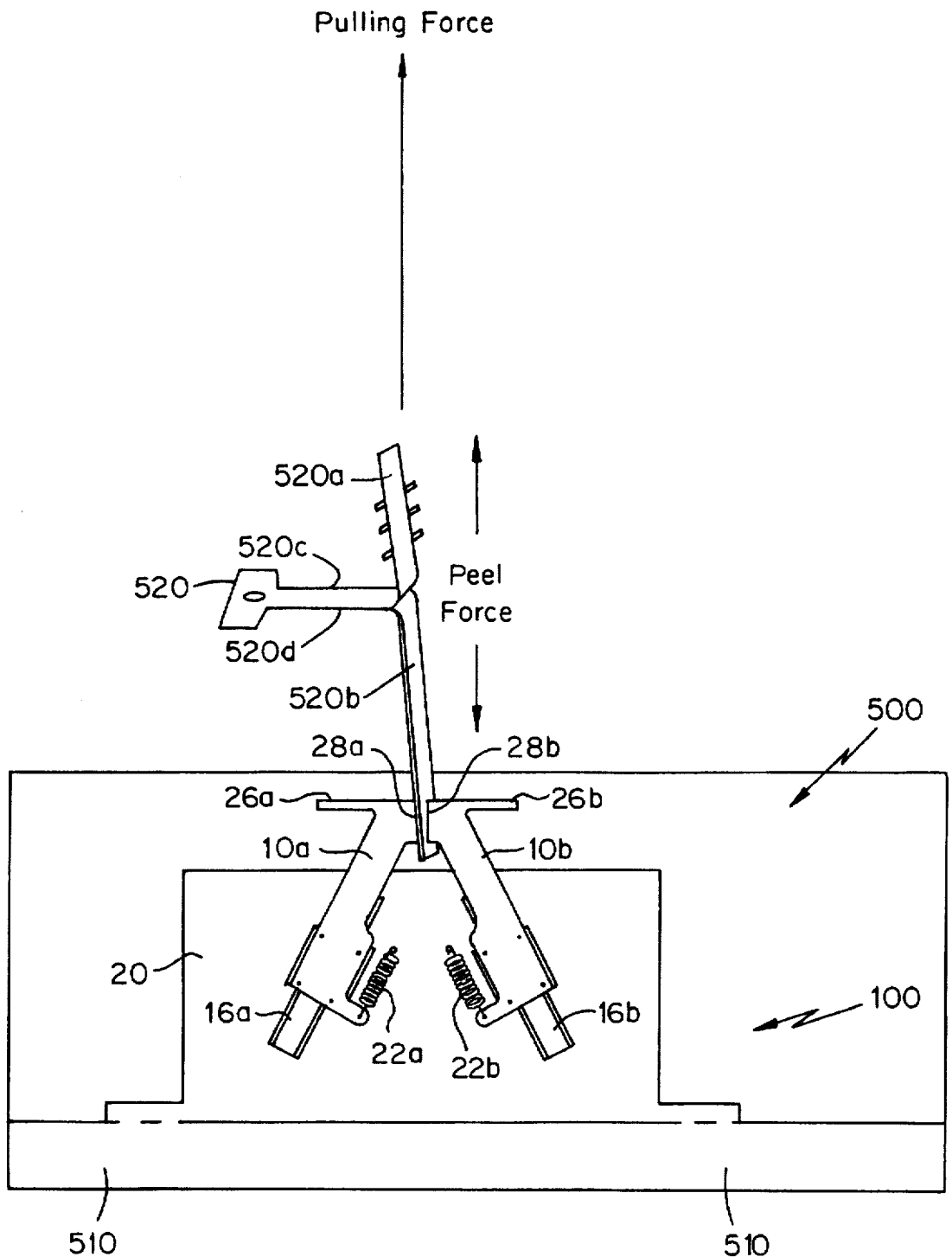
FIG. 5 depicts an arrangement of a clamp assembly of the type shown in FIG. 1 for use in peel testing.

FIG. 5 depicts an arrangement of a clamping device 100 of the type depicted in FIG. 1 for use in peel testing operations. As shown, the base 20 of the clamping assembly 100 is connected by bolts 510 to a stationary support structure 500.

A test specimen 520 is formed of two steel plates 520a and 520b which are welded along seams 520c and 520d. The separated or tongue portion of plate 520b is inserted into the clamp assembly 100 by pressing down on the clamp assembly ears 26a and 26b to separate the respective clamp members 10a and 10b to accept the tongue portion of the plate 520b. Once the tongue has been moved between the jaws 28a and 28b of the clamp assembly 100, the force is removed from the clamp assembly ears 26a and 26b and the respective clamp members 10a and 10b are urged by springs 22a and 22b to slide along the respective linear movement guides 16a and 16b to engage the tongue portion of plate 520b.

As shown, a pulling force is applied to the tongue portion of plate 520a while the stationary clamp assembly 100 grips the tongue portion of plate 520b, resulting in a peel force on the test specimen 520. As the pulling force increases, the respective clamp members 10a and 10b may be pulled further along the respective liner movement guides 16a and 16b. Because the guides 16a and 16b have intersecting axes, this movement of the clamping members 10a and 10b as the force on the test specimen 520 increases, will result in the clamp jaws 28a and 28b moving closer together and hence, exerting a greater clamping force on the tongue of the plate 520b. Accordingly, the grip will automatically increase as the force on the test specimen increases. This will be true whether a serrated, friction or other type grip is utilized.

Figure 6:
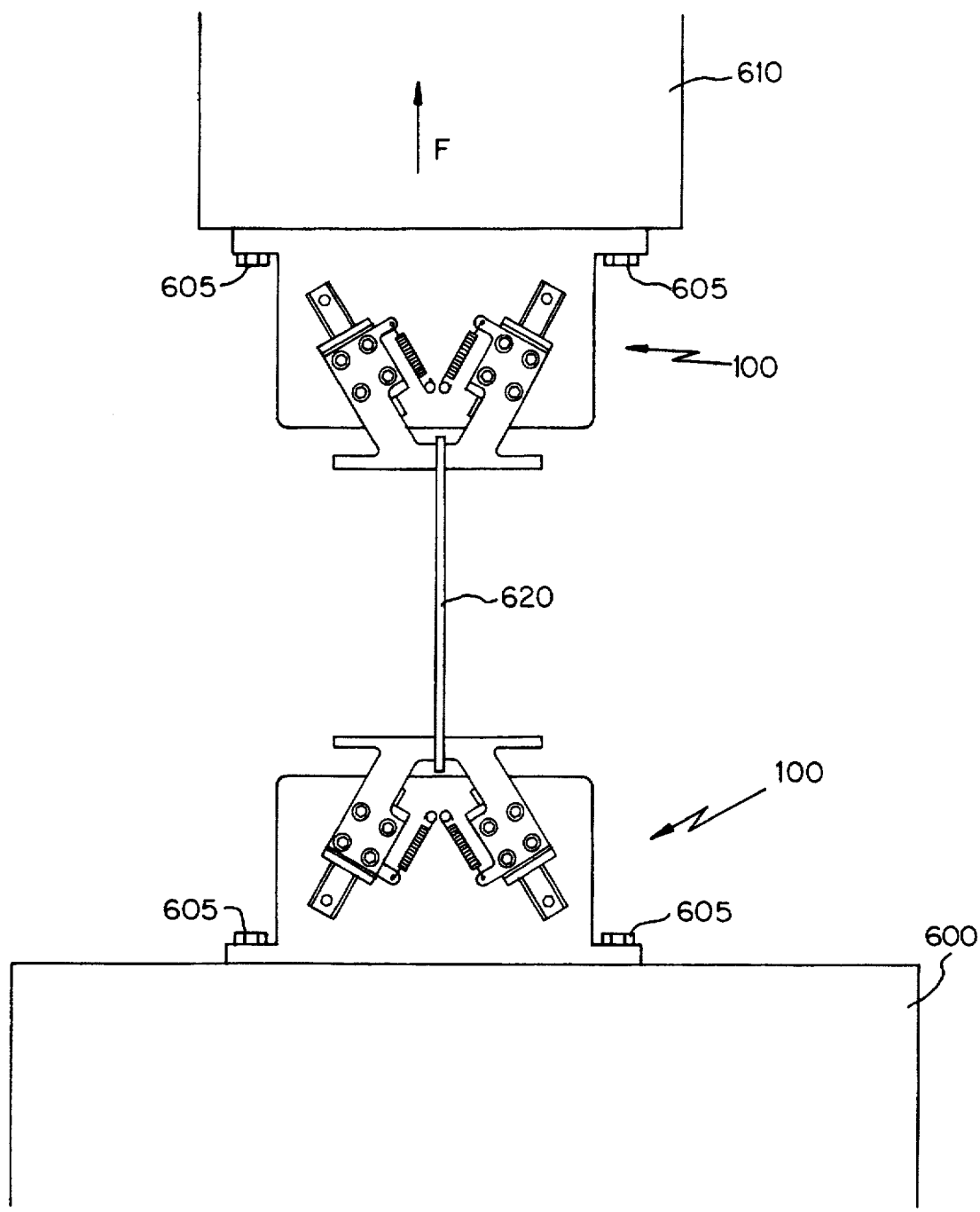
FIG. 6 depicts another arrangement having two clamp assemblies of the type shown in FIG. 1, arranged for use in tension testing a test specimen.

Referring now to FIG. 6, a further arrangement utilizing two clamping devices 100, each identical to the clamping device depicted in FIG. 1, is shown. This arrangement is particularly suitable for tensioning a test specimen 620.

As depicted, one of the clamping assemblies 100 is connected by bolts 605 to a stationary structure 600. The other clamping assembly 100 is connected by bolts 605 to a movable structure 610 which pulls the latter clamping assembly 100 in a vertically upward direction to apply the force "F" to tension the test specimen 620.

It will be recognized that, if desired, the orientation of the respective clamping assemblies 100 could be reversed such that the jaws and ears of the clamping assemblies 100 would be disposed proximate to the structures 600 and 610. In this orientation, movement of the structure 610 in a vertically downward direction would result in the direction of the force "F" being reversed from that indicated in FIG. 6, and a compression load being applied to the test specimen 620. Because of the reversed orientation of the clamp assemblies 100, the grip of the clamp assemblies 100 on the test specimen 620 would automatically increase as the compression force increases.

As described above, an improved clamping device is provided which is suitable for use in gripping test specimens during testing. The described device is capable of use for both tensile and compression testing of test specimens and is particularly suitable for use in peel testing a test specimen. The described clamping device automatically increases its grip as the force on the clamped object increases and yet is simple to operate and easily engaged to and disengaged from the gripped object.

We claim:

1. A clamp assembly for holding an object, comprising:
    a first clamp member having a first grip portion;
    a second clamp member having a second grip portion disposed opposite said first grip portion;
    a first guide member for restricting movement of said first clamp member to movement along a first axes;
    a second guide member for restricting movement of said second clamp member to movement along a second axis, the second axis being disposed so as to cross said first axis at a crossover point;
    a first elastic member connected to said first clamp member and configured to apply a force to urge said first clamp member alonq said first axes and towards the crossover point; and
    a second elastic member connected to said second clamp member and configured to apply a force to urge said second clamp member along said second axes and towards the crossover point.

2. The clamp assembly according to claim 1, further comprising:
    a base, wherein said first guide member and said second guide member are fixedly connected to said base, and said first clamp member is slidingly mounted to said first guide member and said second clamp member is slidingly mounted to said second guide member.

3. The clamp assembly according to claim 2, wherein: said base is a stationary base.

4. The clamp assembly according to claim 1, wherein: at least one of the first and second grip positions is provided with a serrated object-contacting surface to generate a positive grip on an object clamped thereat.

5. The clamp assembly according to claim 3, wherein: said first elastic member and said second elastic member are configured to cause said first grip portion to contact said second grip portion.

6. The clamp assembly according to claim 1, wherein: said first and said second clamp members are configured such that movement of said first clamp member along said first guide member towards said crossover point and said second clamp members along said second guide member towards said crossover point decreases a distance between said first grip portion and said second grip portion.

7. The clamp assembly according to claim 1, wherein:
said first and said second clamp members are configured to be respectively moveable along said first and said second guide members towards said crossover point to cause the first grip portion to come into contact with the second grip portion.

8. The clamp assembly according to claim 1, wherein:
said second axis intersects said first axis at an angle of approximately 60 degrees.

9. The clamp assembly according to claim 1, wherein:
said first clamp member is freely moveable along said first guide member and said second clamp member is freely moveable along said second guide member.

10. A The clamp assembly according to claim 1, further comprising:
a first ear member connected to said first clamp member and configured to receive a first force which urges said first clamp member along said first axes and away from the crossover point; and
a second ear member connected to said second clamp member and configured to receive a second force which urges said second clamp member along said second axes and away from the crossover point.

11. The clamp assembly according to claim 10, wherein:
said first ear member and said second ear member are configured to receive respective forces which cause said first clamp member to slide on said first guide member away from said crossover point and said second clamp member to slide on said second guide member away from said crossover point, to thereby cause said first grip portion to separate from said second grip portion.

12. A method of clamping an object, comprising the steps of:
disposing the object between a first grip portion of a first clamping member and an opposed second grip portion of a second clamping member; and
applying a force to the object along a first direction so as to thereby urge simultaneous linear movement of said first clamping member along a first axes and of said second clamping member along a second axes which crosses the first axes at a crossover point,
wherein said simultaneous urged movements of the first and the second clamping members are both directed towards the crossover point of the first and the second axes.

13. The method according to claim 12, comprising the further step of:
biasing said first clamping member and said second clamping member such that said first grip portion and said second grip portion are constantly urged toward each other.

14. The method according to claim 12, wherein:
the simultaneous linear movement of said first and said second clamping members results in said first and said second grip portions providing enhanced gripping of the object.

15. The method according to claim 12, further comprising the steps of:
applying a release force, in a second direction substantially opposite to the first direction, to thereby cause a first linear movement of said first clamping member along the first axes and a second linear movement of said second clamping member along the second axes,
said first and second linear movements being away from the crossover point of the first and the second axes.

16. The method according to claim 12, wherein:
said first force is one of a tensioning force or a compressing force on the object.

17. A clamp assembly, comprising:
a base;
a first substantially straight guide member mounted to said base and having a first longitudinal axes;
a second substantially straight guide member mounted to said base and having a second longitudinal axes which intersects the first longitudinal axes;
a first clamp member, having a first jaw, slidably mounted to said first guide member so as to be freely moveable only along said first longitudinal axes;
a second clamp member, having a second jaw slidably mounted to said second guide member so as to be freely moveable only along said second longitudinal axes;
a first spring having one end connected to said first clamp member and another end connected to said base, and configured to apply a force to urge the first clamp member in a direction parallel to the first longitudinal axes and towards the intersection of the first and the second longitudinal axes; and
a second spring having one end connected to said second clamp member and another end connected to said base, and configured to apply a force to urge the second clamp member in a direction parallel to the second longitudinal axes and towards the intersection of the first and the second longitudinal axes.

18. The clamp assembly according to claim 17, wherein:
the first and the second springs are configured to respectively apply a substantially equal force responsive to which the first and the second jaws engage an object to be gripped.

19. The clamp assembly according to claim 17, wherein:
said first and said second clamp members are configured to automatically move closer to the intersection of the first and the second longitudinal axes as a force on an object disposed between and engaged by the first and the second jaws is increased.

20. The clamp assembly according to claim 17, wherein:
said first clamp member includes a first ear configured to receive a first force directed away from the intersection of the first and the second longitudinal axes; and
said second clamp member includes a second ear configured to receive a second force directed away from the intersection of the first and the second longitudinal axes,
wherein, said first and said second ears are each configured such that the received forces urge said first clamp member to slide on said first guide member away from the intersection of the first and the second longitudinal axes and said second clamp member to slide on said second guide member away from the intersection of the first and the second longitudinal axes, to thereby increase a distance between said first jaw and said second jaw.

21. The clamp assembly according to claim 17, wherein:
at least one of the first and second jaws is provided with a serrated object-contacting surface to generate a positive grip on an object clamped thereat.

22. The method according to claim 12, wherein:
at least one of the first and second grip positions is provided with a serrated object-contacting surface to generate a positive grip on an object clamped thereat.

* * * * *